United States Patent [19]

Keil et al.

[11] Patent Number: 4,898,610
[45] Date of Patent: Feb. 6, 1990

[54] CYCLOHEXANE-1,3-DIONE DERIVATIVES AND THEIR USE FOR CONTROLLING UNDESIRABLE PLANT GROWTH

[75] Inventors: Michael Keil, Freinsheim; Dieter Jahn, Edingen-Neckarhausen; Rainer Becker, Bad Duerkheim; Wolfgang Rohr, Wachenheim; Bruno Wuerzer, Otterstadt, all of Fed. Rep. of Germany

[73] Assignee: BASF Aktiengesellschaft, Ludwigshafen, Fed. Rep. of Germany

[21] Appl. No.: 4,217

[22] Filed: Jan. 5, 1987

Related U.S. Application Data

[63] Continuation of Ser. No. 639,473, Aug. 10, 1984, abandoned.

[30] Foreign Application Priority Data

Aug. 11, 1983 [DE] Fed. Rep. of Germany ....... 3329017

[51] Int. Cl.$^4$ ............................................. A01N 33/04
[52] U.S. Cl. ..................................... 71/121; 564/256; 71/103; 71/105; 71/111; 560/35; 558/426
[58] Field of Search .................. 564/256; 71/103, 105, 71/121, 111; 560/35; 558/426

[56] References Cited

U.S. PATENT DOCUMENTS 3,950,420 4/1976 Sawaki et al. ...................... 71/106

FOREIGN PATENT DOCUMENTS 0082694 6/1983 European Pat. Off. .
0080301 8/1983 European Pat. Off. .
0085529 8/1983 European Pat. Off. .
0085530 8/1983 European Pat. Off. .
1461170 1/1977 United Kingdom .

OTHER PUBLICATIONS

Chemical Abstracts, vol. 86, p. 397 16357h.
*Advances in Pesticide Science*, Part 2 (1979), pp. 235–243. Pergamon Press, Publ.

Primary Examiner—James H. Reamer
Attorney, Agent, or Firm—Keil & Weinkauf

[57] ABSTRACT

Cyclohexane-1,3-dione derivatives of the formula

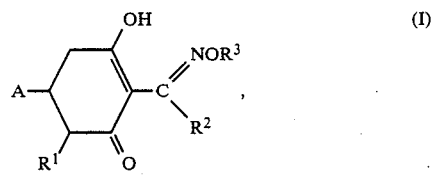

where A is phenyl which is monosubstituted in the ortho- or meta-position by alkoxy, nitro, halogen or methylsulfonyl, or is phenyl which is monosubstituted in the ortho-, meta- or para-position by alkyl, phenyl, alkoxy, fluorine-substituted alkoxy, unsubstituted or substituted phenoxy, alkenyloxy, alkynyloxy, unsubstituted or substituted benzyloxy, alkylsulfinyl, alkylsulfonyl, alkylsulfonyloxy, trifluoromethyl, alkoxyalkyl or alkoxyalkoxy, or is phenyl which is disubstituted trisubstituted or tetrasubstituted by identical or different substituents selected from the group consisting of alkyl, alkoxy, halogen, nitro and 2,4-dichlorophenoxy, with the proviso that, where the substituents are identical, the disubstituted, trisubstituted or tetrasubstituted phenyl radical does not carry methyl radicals, $R^1$ is hydrogen, methoxycarbonyl, ethoxycarbonyl, methyl or cyano, $R^2$ is alkyl, and $R^3$ is alkyl, alkenyl, haloalkenyl or propargyl, or salts of these compounds, and their use for combatting unwanted plant growth.

10 Claims, No Drawings

CYCLOHEXANE-1,3-DIONE DERIVATIVES AND THEIR USE FOR CONTROLLING UNDESIRABLE PLANT GROWTH

This application is a continuation of application Ser. No. 639,473, filed on Aug. 10, 1984 now abandoned.

The present invention relates to cyclohexane-1,3-dione derivatives and to herbicides which contain these compounds as an active ingredient.

It has been disclosed that cyclohexane-1,3-dione derivatives can be used for controlling undesirable grasses in broad-leaved crops (German Laid-Open Application DOS 2,439,104 and European Laid-Open Applications 0080 301 and 0082 694).

We have found that cyclohexane-1,3-dione derivatives of the formula

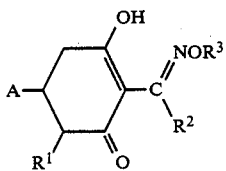
(I)

where A is phenyl which is monosubstituted in the ortho- or meta-position by $C_1$- or $C_2$-alkoxy, nitro, halogen or methylsulfonyl, or is phenyl which is monosubstituted in the ortho-, meta- or para-position by branched $C_3$–$C_5$-alkyl, phenyl, $C_2$–$C_4$-alkoxy, fluorine-substituted $C_1$–$C_3$-alkoxy, unsubstituted, chlorine-substituted, nitro-substituted or trifluoromethyl-substituted phenoxy, $C_3$–$C_5$-alkenyloxy, $C_3$–$C_5$-alkynyloxy, unsubstituted, methyl-substituted, chlorine-substituted or nitro-substituted benzyloxy, $C_1$–$C_4$-alkylsulfinyl, $C_2$- or $C_3$-alkylsulfonyl, $C_1$–$C_3$-alkylsulfonyloxy, trifluoromethyl, $C_2$–$C_5$-alkoxyalkyl or $C_2$–$C_5$-alkoxyalkoxy, or is phenyl which is disubstituted, trisubstituted or tetrasubstituted by identical or different substituents selected from the group consisting of $C_1$–$C_4$-alkyl, $C_1$–$C_4$-alkoxy, halogen, nitro and 2,4-dichlorophenoxy, with the proviso that, where the substituents are identical, the disubstituted, trisubstituted or tetrasubstituted phenyl radical does not carry methyl radicals, $R^1$ is hydrogen, methoxycarbonyl, ethoxycarbonyl, methyl or cyano, $R^2$ is $C_1$–$C_4$-alkyl, and $R^3$ is $C_1$–$C_3$-alkyl, $C_3$- or $C_4$-alkenyl, $C_3$- or $C_4$-haloalkenyl having 1, 2 or 3 halogen substituents, or propargyl, and salts of these compounds have a herbicidal action against grasses, and do not damage either broad-leaved crops or monocotyledonous crops which do not belong to the family of the grasses (gramineae). Moreover, it is also possible to use compounds of the formula I for selectively controlling undesirable grasses in certain species of gramineous crops, such as rice and other cereals.

The compounds of the formula I can occur in several forms, all of which are embraced by the claim:

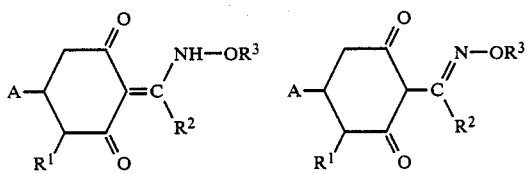

-continued

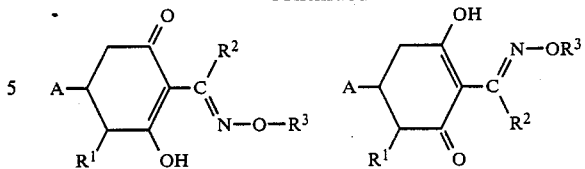

In formula I, A is phenyl which is monosubstituted in the ortho- or meta-position by substituents from the group consisting of $C_1$- or $C_2$-alkoxy, nitro, halogen and methylsulfonyl, or is phenyl which is monosubstituted in the ortho-, meta- or para-position by substituents from the group consisting of branched $C_3$–$C_5$-alkyl, phenyl, $C_2$–$C_4$-alkoxy, fluorine-substituted $C_1$–$C_3$-alkoxy, unsubstituted, chlorine-substituted, nitrosubstituted and trifluoromethyl-substituted phenoxy, $C_3$–$C_5$-alkenyloxy, $C_3$–$C_5$-alkynyloxy, unsubstituted, methyl-substituted, chlorine-substituted and nitro-substituted benzyloxy, $C_1$–$C_3$-alkylsulfinyl, $C_2$- and $C_3$-alkylsulfonyl, $C_1$–$C_8$-alkylsulfonyloxy, trifluoromethyl, $C_2$–$C_5$-alkoxyalkyl and $C_2$–$C_5$-alkoxyalkoxy, or is phenyl which is disubstituted, trisubstituted or tetrasubstituted by substituents selected from the group consisting of $C_1$–$C_4$-alkyl, $C_1$–$C_4$-alkoxy, halogen, eg. chlorine or fluorine, nitro or 2,4-dichlorophenoxy. Examples of these phenyl substituents are methoxy, ethoxy, n-propoxy, t-butoxy, n-butoxy, trifluoromethoxy, difluoromethoxy, 1,1,2,2-tetrafluoroethoxy, n-propyl, n-butyl, isopropyl, t-butyl, but-2-enyloxy, allyloxy, prop-2-ynyloxy, nitro, chlorine, fluorine, phenyl, trifluoromethyl, benzyloxy, p-chlorobenzyloxy, p-methylbenzyloxy, p-nitrobenzyloxy, phenoxy, 2,4-dichlorophenoxy, 2-chloro-4-trifluoromethylphenoxy, 2-chloro-4-nitrophenoxy, methylsulfinyl, ethylsulfinyl, methylsulfonyl, ethylsulfonyl, methylsulfonyloxy, ethylsulfonyloxy, methoxymethyl, ethoxymethyl, 2-ethoxyethyl, 2-methoxyethyl, methoxymethoxy, ethoxymethoxy, 2-methoxyethoxy and 2-ethoxyethoxy. Examples of possible radicals A are 2-methoxyphenyl, 3-nitrophenyl, 2-fluorophenyl, 2-methylsulfonyl, 4-tert.-butylphenyl, biphenyl-4-yl, 4-ethoxyphenyl, 4-difluoromethoxyphenyl, 4-phenoxyphenyl, 4-(prop-2-ynyloxy)-phenyl, 4-allyloxyphenyl, 4-benzyloxyphenyl, 4-methylsulfinylphenyl, 3-trifluoromethylphenyl, 4-methylsulfonyloxyphenyl, 3,4-dimethoxyphenyl, 2-chloro-4-nitrophenyl, 2,6-dichlorophenyl, 2-chloro-6-fluorophenyl, 4-methoxy-3-methylphenyl, 2,3,4-trimethoxyphenyl, 2,4,5-trimethoxyphenyl, 4-methoxy-2,3,6-trimethylphenyl, 4-methoxymethylphenyl and 4-(2-methoxyethoxy)-phenyl.

In formula I, $R^1$ is hydrogen, methoxycarbonyl, ethoxycarbonyl, methyl or cyano, $R^2$ is straight-chain or branched $C_1$–$C_4$-alkyl, i.e. methyl, ethyl, n-propyl, i-propyl, n-butyl, sec.-butyl, i-butyl or tert.-butyl, and $R^3$ is propargyl, $C_1$–$C_3$-alkyl, $C_3$- or $C_4$-alkenyl, or $C_3$ or $C_4$-haloalkenyl which can contain one, two or three halogen substituents, eg. methyl, ethyl, n-propyl, i-propyl, n-butyl, sec.-butyl, i-butyl, tert.-butyl, allyl, 1-chloroprop-1-en-3-yl, 2-chloroprop-1-en-3-yl, 1,3-dichloroprop-1-en-3-yl or 1,1,2-trichloroprop-1-en-3-yl.

Examples of suitable salts of the compounds of the formula I are the alkali metal salts, in particular the potassium or sodium salts, alkaline earth metal salts, in particular calcium, magnesium or barium salts, manganese, copper, zinc and iron salts, and ammonium and phosphonium salts, eg. alkylammonium, dialkylammonium, trialkylammonium, tetraalkylammonium, benzyltrialkylammonium and triphenylphosphonium salts, and trialkylsulfonium and trialkylsulfoxonium salts.

Preferred cyclohexane-1,3-dione derivatives of the formula I are those in which A is phenyl which is monosubstituted in the ortho-, meta- or para-position by fluorine-substituted $C_1$-$C_3$-alkoxy, $C_3$-$C_5$-alkenyloxy or $C_3$-$C_5$-alkynyloxy, or those in which A is phenyl which is substituted by trifluoromethyl, in particular 4-trifluoromethylphenyl. Furthermore, in formula I, $R^1$ is preferably hydrogen.

The compounds of the formula I can be obtained by reacting a compound of the formula

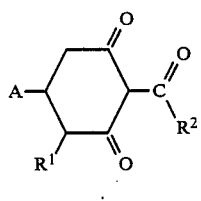

(II)

where A, $R^1$ and $R^2$ have the above meanings, with a hydroxylamine derivative $R^3O$—$NH_3Y$, where $R^3$ has the above meanings and Y is an anion.

The reaction is advantageously carried out in the heterogeneous phase in an inert diluent at from 0° to 80° C. or at from 0° C. to the boiling point of the reaction mixture, in the presence of a base. Examples of suitable bases are carbonates, bicarbonates, acetates, alcoholates, hydroxides and oxides of alkali metals and alkaline earth metals, in particular of sodium, potassium, magnesium and calcium. It is also possible to use organic bases, such as pyridine or tertiary amines.

The reaction proceeds particularly readily at a pH of from 2 to 9, in particular from 4.5 to 5.5. The pH is advantageously established by adding an acetate, for example an alkali metal acetate, in particular sodium acetate or potassium acetate, or a mixture of the two salts. Alkali metal acetates are added in an amount of, for example, from 0.5 to 2 moles, based on the ammonium compound of the formula $R^3O$—$NH_3Y$.

Examples of suitable solvents are dimethyl sulfoxide, alcohols, such as methanol, ethanol or isopropanol, benzene, hydrocarbons and chlorohydrocarbons, such as chloroform, dichloroethane, hexane or cyclohexane, esters, such as ethyl acetate, and ethers, such as dioxane or tetrahydrofuran.

The reaction is complete after a few hours, and the product can then be isolated by evaporating down the mixture, adding water, extracting with a non-polar solvent, such as methylene chloride, and distilling off the solvent under reduced pressure.

The compounds of the formula I can furthermore be obtained by reacting a compound of the formula II with a hydroxylamine of the formula $R^3O$—$NH_2$, where $R^3$ has the above meanings, in an inert diluent at from 0° C. to the boiling point of the reaction mixture, in particular from 15° to 70° C. If necessary, the hydroxylamine can be employed in the form of an aqueous solution.

Examples of suitable solvents for this reaction are alcohols, such as methanol, ethanol, isopropanol or cyclohexanol, hydrocarbons and chlorohydrocarbons, such as hexane, cyclohexane, methylene chloride, toluene or dichloroethane, esters, such as ethyl acetate, nitriles, such as acetonitrile, and cyclic ethers, such as tetrahydrofuran.

The alkali metal salts of the compounds of the formula I can be obtained by treating these compounds with sodium hydroxide or potassium hydroxide in aqueous solution or in an organic solvent, eg. methanol, ethanol or acetone. The base used may also be a sodium alcoholate or potassium alcoholate.

The other metal salts, eg. the manganese, copper, zinc, iron, calcium, magnesium and barium salts, can be prepared from the sodium salts by reaction with the appropriate metal chlorides in aqueous solution. Ammonium, phosphonium, sulfonium and sulfoxonium salts can be prepared by reacting a compound of the formula I with ammonium, phosphonium, sulfonium or sulfoxonium hydroxide, if necessary in aqueous solution.

The compounds of the formula II can be prepared, by a conventional method (Tetrahedron Lett. 29 (1975), 2,491), from cyclohexane-1,3-diones of the formula III, which likewise can occur in the tautomeric forms of the formulae IIIa and IIIb

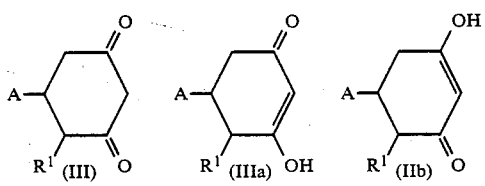

It is also possible to prepare compounds of the formula II via the enol-ester intermediates; these are obtained in the conversion of compounds of the formula II, possibly as an isomer mixture, and undergo rearrangement in the presence of an imidazole or pyridine derivative (Japanese Preliminary Published Application 79/063052).

The compounds of the formula III are obtained by a conventional method, as is evident from the equations below:

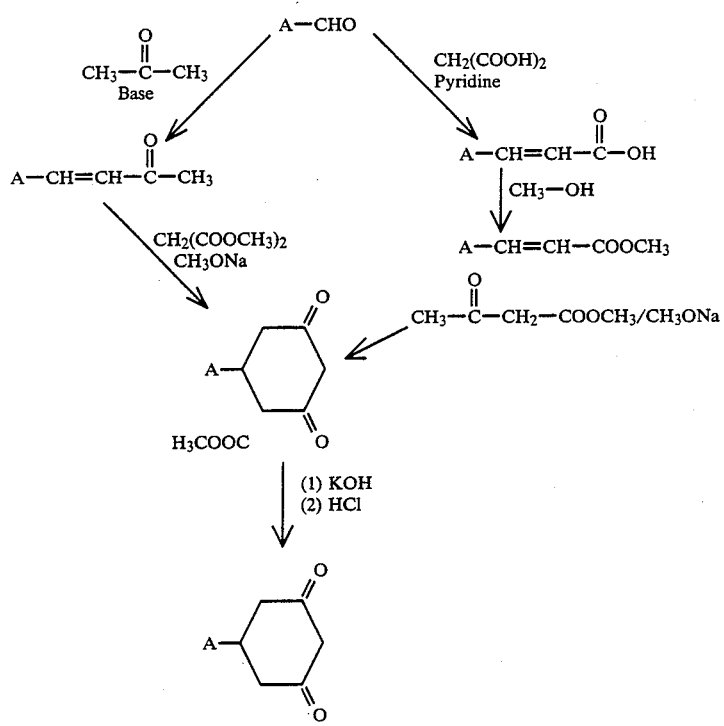

The aldehydes A—CHO, which are used as starting compounds, can be prepared by a conventional method, for example Vilsmeier formylation, oxidation of alcohols, reduction of carboxylic acid derivatives, etc. The Example which follows illustrates the preparation of the cyclohexane-1,3-dione derivatives of the formula I. In this Example, parts by weight bear the same relation to parts by volume as that of the kilogram to the liter.

EXAMPLE 1

7.0 parts by weight of 2-butyryl-5-(4-phenoxyphenyl)-cyclohexane-1,3-dione were dissolved in 50 parts by volume of methanol, and 2.15 parts by weight of ethoxyammonium chloride and 1.85 parts by weight of sodium bicarbonate were added to this mixture. The mixture was stirred for 12 hours at room temperature, after which it is evaporated down under reduced pressure, the residue was stirred with 100 parts of dichloromethane and 100 parts of water, the organic phase was separated off, the aqueous phase was extracted with 50 parts of dichloromethane, and the combined organic phases were washed with water, dried over sodium sulfate and evaporated down under reduced pressure.

6.9 parts of 2-(1-ethoxyaminobutylidene)-5-(4-phenoxyphenyl)-cyclohexane-1,3-dione ($n_D^{22}=1.5670$; active ingredient No. 76) were obtained.

$C_{24}H_{27}NO_4$ (393) Calculated: C 73.26, H 6.92, N 3.56. Found: C 72.7, H 7.0, N 3.5.

| Active ingredient no. | A | $R^1$ | $R^2$ | $R^3$ | $n_D(°C.)/m.p.[°C.]$ |
|---|---|---|---|---|---|
| 1 | 2-methoxyphenyl | $COOCH_3$ | $n-C_3H_7$ | $C_2H_5$ | |
| 2 | " | " | " | $CH_2=CH-CH_2$ | |
| 3 | " | " | $C_2H_5$ | " | |
| 4 | " | " | " | $C_2H_5$ | |
| 5 | " | H | $n-C_3H_7$ | " | 1.5509 (23) |
| 6 | " | H | " | $CH_2=CH-CH_2$ | 1.5489 (23) |
| 7 | " | H | $C_2H_5$ | $C_2H_5$ | 1.5612 (20) |
| 8 | " | H | " | $CH_2=CH-CH_2$ | 1.5631 (20) |
| 9 | 2-ethoxphenyl | H | $n-C_3H_7$ | " | |
| 10 | " | H | " | $C_2H_5$ | |
| 11 | 3-methoxyphenyl | $COOCH_3$ | " | $CH_2=CH-CH_2$ | |
| 12 | " | " | $C_2H_5$ | " | |
| 13 | " | H | $n-C_3H_7$ | $C_2H_5$ | |
| 14 | 3-methoxyphenyl | H | $C_2H_5$ | $C_2H_5$ | 1.5378 (28) |
| 15 | " | H | " | $CH_2=CH-CH_2$ | 1.5552 (25) |
| 16 | 3-ethoxyphenyl | H | $n-C_3H_7$ | $C_2H_5$ | |
| 17 | " | H | " | $CH_2=CH-CH_2$ | |
| 18 | 2-nitrophenyl | H | " | " | |
| 19 | " | H | " | $C_2H_5$ | |
| 20 | 3-nitrophenyl | $COOCH_3$ | $n-C_3H_7$ | $C_2H_5$ | |
| 21 | " | " | " | $CH_2=CH-CH_2$ | |
| 22 | " | " | $C_2H_5$ | $C_2H_5$ | |
| 23 | " | " | " | $CH_2=CH-CH_2$ | |
| 24 | " | H | $n-C_3H_7$ | $C_2H_5$ | |
| 25 | " | H | " | $CH_2=CH-CH_2$ | 1.5645 (23) |

-continued

| | | | | | |
|---|---|---|---|---|---|
| 26 | " | H | C₂H₅ | C₂H₅ | 1.5672 (23) |
| 27 | " | H | " | CH₂=CH—CH₂ | 1.5648 (25) |
| 28 | 2-chlorophenyl | H | n-C₃H₇ | C₂H₅ | 47 |
| 29 | " | H | " | CH₂=CH—CH₂ | |
| 30 | 2-fluorophenyl | H | " | C₂H₅ | 47–50 |
| 31 | " | H | " | CH₂=CH—CH₂ | 36 |
| 32 | 3-fluorophenyl | H | " | C₂H₅ | 1,5452 (24) |
| 33 | " | H | " | CH₂=CH—CH₂ | |
| 34 | 2-methylsulfonylphenyl | H | " | " | |
| 35 | " | H | " | C₂H₅ | |
| 36 | 3-methylsulfonylphenyl | H | " | " | |
| 37 | " | H | " | CH₂=CH—CH₂ | |
| 38 | 4-isopropylphenyl | H | " | " | |
| 39 | " | COOCH₃ | " | " | |
| 40 | " | H | " | C₂H₅ | |
| 41 | 4-tert.-butylphenyl | H | n-C₃H₇ | CH₂=CH—CH₂ | 60–64 |
| 42 | " | H | " | C₂H₅ | 50–52 |
| 43 | 4-tert.-butylphenyl | COOCH₃ | n-C₃H₇ | CH₂=CH—CH₂ | 62–66 |
| 44 | " | " | " | C₂H₅ | |
| 45 | biphenyl-4-yl | " | " | " | 88 |
| 46 | " | " | " | CH₂=CH—CH₂ | |
| 47 | " | H | " | C₂H₅ | 88 |
| 48 | " | H | " | CH₂=CH—CH₂ | 54 |
| 49 | 4-ethoxyphenyl | H | " | C₂H₅ | 57–61 |
| 50 | " | H | " | CH₂=CH—CH₂ | 55 |
| 51 | " | H | C₂H₅ | " | 67–70 |
| 52 | " | H | " | C₂H₅ | 69–71 |
| 53 | 4-tert.-butoxyphenyl | H | n-C₃H₇ | " | |
| 54 | " | H | " | CH₂=CH—CH₂ | |
| 55 | 4-difluoromethoxy-phenyl | COOCH₃ | n-C₃H₇ | C₂H₅ | 1.5248 (25) |
| 56 | " | " | " | H—C≡C—CH₂ | 1.5315 (25) |
| 57 | " | " | C₂H₅ | CH₂=CH—CH₂ | 1.5330 (28) |
| 58 | " | " | " | n-C₃H₇ | 1.5252 (28) |
| 59 | " | H | " | C₂H₅ | 65–67 |
| 60 | " | H | " | n-C₃H₇ | 54–56 |
| 61 | " | H | " | HC≡C—CH₂ | 64–66 |
| 62 | " | H | n-C₃H₇ | n-C₃H₇ | 70–72 |
| 63 | 4-(1,1,2,2-tetra-fluoroethoxy)-phenyl | COOCH₃ | " | CH₂=CH—CH₂ | |
| 64 | " | H | " | C₂H₅ | 47 |
| 65 | " | H | " | CH₂=CH—CH₂ | |
| 66 | 4-(1,1,2,2-tetrafluoro-ethoxy)-phenyl | H | C₂H₅ | CH₂=CH—CH₂ | 58 |
| 67 | " | H | " | C₂H₅ | 81–84 |
| 68 | 3-(1,1,2,2-tetra-fluoroethoxy)-phenyl | COOCH₃ | n-C₃H₇ | CH₂=CH—CH₂ | |
| 69 | " | " | " | C₂H₅ | |
| 70 | " | H | " | " | |
| 71 | " | H | " | CH₂=CH—CH₂ | |
| 72 | 3-(2-chloro-4-tri-fluoromethylphenoxy)-phenyl | H | " | " | 1.5475 (25) |
| 73 | 4-(2-chloro-4-nitro-phenoxy)-phenyl | H | " | C₂H₅ | |
| 74 | " | H | " | CH₂=CH—CH₂ | |
| 75 | 4-phenoxyphenyl | H | " | " | 1.5816 (22) |
| 76 | " | H | " | C₂H₅ | 1.5670 (22) |
| 77 | " | H | C₂H₅ | " | |
| 78 | " | H | " | CH₂=CH—CH₂ | |
| 79 | 4-(prop-2-inoxy)-phenyl | H | n-C₃H₇ | C₂H₅ | 1.5458 (28) |
| 80 | " | H | " | CH₂=CH—CH₂ | 1.5645 (28) |
| 81 | " | H | " | n-C₃H₇ | 1.5518 (28) |
| 82 | 4-(prop-2-inoxy)-phenyl | H | C₂H₅ | C₂H₅ | |
| 83 | " | H | " | CH₂=CH—CH₂ | 1.5722 (28) |
| 84 | " | H | " | n-C₃H₇ | |
| 85 | " | H | " | CH≡C—CH₂ | |
| 86 | 4-allyloxyphenyl | H | n-C₃H₇ | C₂H₅ | 54–57 |
| 87 | " | H | " | CH₂=CH—CH₂ | 53–57 |
| 88 | " | H | CH₂=CH—CH₂ | C₂H₅ | |
| 89 | " | H | C₂H₅ | " | |
| 90 | 2-(but-2-enyloxy)-phenyl | H | n-C₃H₇ | " | |
| 91 | " | H | " | CH₂=CH—CH₂ | |
| 92 | 4-benzyloxyphenyl | H | " | C₂H₅ | 54–57 |
| 93 | " | H | " | CH₂=CH—CH₂ | |
| 94 | 4-(p-chlorobenzyloxy)-phenyl | H | " | " | 78–80 |
| 95 | " | H | " | C₂H₅ | 120–123 |
| 96 | 4-(p-methylbenzyloxy)- | H | " | CH₂=CH—CH₂ | 99–102 |

-continued

| | | | | | |
|---|---|---|---|---|---|
| 97 | phenyl | H | " | C₂H₅ | 82–83 |
| 98 | 4-(p-nitrobenzyloxy)-phenyl | H | " | " | |
| 99 | " | H | " | CH₂=CH—CH₂ | |
| 101 | 4-methylsulfinylphenyl | H | " | C₂H₅ | |
| 102 | 4-methylsulfinylphenyl | H | n-C₃H₇ | CH₂=CH—CH₂ | |
| 103 | 4-ethylsulfonylphenyl | H | " | C₂H₅ | |
| 104 | " | H | " | CH₂=CH—CH₂ | |
| 105 | 2-ethylsulfonylphenyl | H | " | " | |
| 106 | " | H | " | C₂H₅ | |
| 107 | 3-trifluoromethyl-phenyl | COOCH₃ | n-C₃H₇ | CH₂=CH—CH₂ | |
| 108 | " | " | " | C₂H₅ | |
| 109 | 4-trifluoromethylphenyl | H | " | " | 65–67 |
| 110 | " | H | " | CH₂=CH—CH₂ | |
| 111 | " | H | C₂H₅ | " | |
| 112 | " | H | " | C₂H₅ | 68–71 |
| 113 | 4-methylsulfonyloxy-phenyl | COOCH₃ | n-C₃H₇ | CH₂=CH—CH₂ | |
| 114 | " | " | " | C₂H₅ | |
| 115 | 2,4-dimethoxyphenyl | H | C₂H₅ | C₂H₅ | 81–82 |
| 116 | " | H | " | CH₂=CH—CH₂ | 73–74 |
| 117 | 2,4-dimethoxyphenyl | COOCH₃ | n-C₃H₇ | C₂H₅ | 1.5321 (23) |
| 118 | " | " | " | CH₂=CH—CH₂ | 1.5432 (23) |
| 119 | " | H | " | C₂H₅ | 92 |
| 120 | " | H | " | CH₂=CH—CH₂ | |
| 121 | 3,4-dimethoxyphenyl | H | " | C₂H₅ | |
| 122 | " | H | " | CH₂=CH—CH₂ | 1.5561 (22) |
| 123 | " | H | C₂H₅ | " | " |
| 124 | " | H | " | C₂H₅ | |
| 125 | 2-chloro-4-nitrophenyl | COOCH₃ | C₂H₅ | C₂H₅ | 105–106 |
| 126 | " | " | " | CH₂=CH—CH₂ | |
| 127 | " | H | n-C₃H₇ | C₂H₅ | 119–121 |
| 128 | " | H | " | CH₂=CH—CH₂ | 80–82 |
| 129 | " | H | C₂H₅ | C₂H₅ | 125–126 |
| 130 | " | H | " | CH₂=CH—CH₂ | |
| 131 | 3,4-dichlorophenyl | H | n-C₃H₇ | CH₂=CH—CH₂ | |
| 132 | " | COOCH₃ | " | " | |
| 133 | methoxy-3-methyl- | " | " | " | C₂H₅ |
| 134 | " | H | " | " | |
| 135 | 2,4-dichlorophenyl | COOCH₃ | " | CH₂=CH—CH₂ | |
| 136 | " | " | " | C₂H₅ | |
| 137 | " | H | " | CH₂=CH—CH₂ | 75 |
| 138 | " | H | " | C₂H₅ | 102 |
| 139 | 2,6-dichlorophenyl | H | " | " | 1.5760 (21) |
| 140 | " | H | " | CH₂=CH—CH₂ | |
| 141 | 2-chloro-6-fluorophenyl | H | " | C₂H₅ | 1.5532 (26) |
| 142 | " | H | " | CH₂=CH—CH₂ | 1.5575 (26) |
| 143 | 4-methoxy-3-methylphe-nyl phenyl | H | n-C₃H₇ | CH₂=CH—CH₂ | |
| 144 | " | H | " | C₂H₅ | |
| 145 | " | H | C₂H₅ | " | |
| 146 | " | H | " | CH₂=CH—CH₂ | |
| 147 | 4-(2,4-dichlorophenoxy)-3-nitrophenyl | COOCH₃ | n-C₃H₇ | CH₂=CH—CH₂ | |
| 148 | " | " | " | C₂H₅ | |
| 149 | 2,3,4-trimethoxyphenyl | H | " | " | 70–71 |
| 150 | " | H | " | n-C₃H₇ | 1.5325 (26) |
| 151 | " | H | " | CH₂=CH—CH₂ | 1.5424 (26) |
| 152 | " | H | C₂H₅ | C₂H₅ | 50 |
| 153 | " | H | " | n-C₃H₇ | 1.5449 (22) |
| 154 | " | H | " | CH₂=CH—CH₂ | 1.5555 (22) |
| 155 | 2,4,5-trimethoxyphenyl | H | C₂H₅ | C₂H₅ | 1.5552 (26) |
| 156 | " | H | " | n-C₃H₇ | 1.5482 (26) |
| 157 | " | H | " | CH₂=CH—CH₂ | 1.5581 (26) |
| 158 | 3,4,5-trimethoxyphenyl | H | " | " | |
| 159 | " | H | " | C₂H₅ | |
| 160 | " | H | n-C₃H₇ | " | |
| 161 | " | H | " | CH₂=CH—CH₂ | |
| 162 | 4-methoxy-2,3,6-tri-methylphenyl | H | " | C₂H₅ | 1.5506 (24) |
| 163 | " | H | " | n-C₃H₇ | |
| 164 | " | H | " | H—C≡C—CH₂ | 1.5600 (24) |
| 165 | " | H | " | ClCH=CH—CH₂ | 1.5625 (24) |
| 166 | 4-methoxy-2,3,6-tri-methylphenyl | H | C₂H₅ | C₂H₅ | 1.5572 (24) |
| 167 | " | H | " | CH₂=CH—CH₂ | 1.5602 (24) |
| 168 | " | H | " | n-C₃H₇ | |
| 169 | 4-methoxymethylphenyl | H | n-C₃H₇ | CH₂=CH—CH₂ | 1.5501 (23) |
| 170 | " | H | " | C₂H₅ | |

-continued

| | | | | | |
|---|---|---|---|---|---|
| 171 | 4-methoxymethylphenyl | H | n-C$_3$H$_7$ | n-C$_3$H$_7$ | 34–35 |
| 172 | " | H | C$_2$H$_5$ | C$_2$H$_5$ | |
| 173 | " | H | " | CH$_2$=CH—CH$_2$ | |
| 174 | 4-methoxyethoxyphenyl | H | n-C$_3$H$_7$ | " | |
| 175 | " | H | " | C$_2$H$_5$ | 62–64 |
| 176 | 4-methoxymethoxyphenyl | H | n-C$_3$H$_7$ | " | |
| 177 | " | H | " | CH$_2$=CH—CH$_2$ | |
| 179 | 2-(but-2-enyloxy)-phenyl | H | n-C$_3$H$_7$ | n-C$_3$H$_7$ | viscous oil |
| 180 | 2-(but-2-enyloxy)-phenyl | H | C$_2$H$_5$ | C$_2$H$_5$ | 1.5561 (25) |
| 181 | 2-(but-2-enyloxy)-phenyl | H | C$_2$H$_5$ | allyl | 1.5620 (25) |
| 182 | 2-(but-2-enyloxy)-phenyl | H | C$_2$H$_5$ | n-C$_3$H$_7$ | 1.5519 (25) |
| 183 | 3-methoxy-phenyl | COOCH$_3$ | C$_2$H$_5$ | C$_2$H$_5$ | 1.5378 (28) |
| 184 | 3-phenoxy-phenyl | H | n-C$_3$H$_7$ | allyl | viscous oil |
| 185 | 3,5-dichlorophenyl | H | n-C$_3$H$_7$ | C$_2$H$_5$ | 1.5684 (25) |
| 186 | 3,5-dichlorophenyl | H | n-C$_3$H$_7$ | allyl | 1.5778 (25) |
| 187 | 4-methoxy-3-nitrophenyl | H | n-C$_3$H$_7$ | C$_2$H$_5$ | 71–73 |
| 188 | 4-trifluoromethyl-phenyl | H | CH$_3$ | C$_2$H$_5$ | 67–70 |
| 189 | 4-trifluoromethyl-phenyl | H | CH$_3$ | allyl | 58–60 |
| 190 | 3-methyl-4-nitro-phenyl | H | n-C$_3$H$_7$ | ethyl | |

$^1$H—NMR spectroscopic data; chemical shift in
σ values [ppm] in CDCl$_3$, based on tetramethylsilane as
internal standard.
Abbreviations for signal structures:
s = Singlet   d = doublet
q = quartet   m = multiplet

| Compound no. | —NH—O—CH$_2$— | |
|---|---|---|
| 1 | 4.11 (q) | 3.87 CH$_3$O |
| 3 | 4.52 (d) | 3.84 CH$_3$O |
| 11 | 4.54 (d) | 6.8 (m); 7.2 (m) H$_{arom.}$ |
| 20 | 4.13 (s) | 7.6 (m); 8.1 (m) H$_{arom.}$ |
| 38 | 4.55 (d) | 7.15 (m) H$_{arom.}$ |
| 53 | 4.10 (q) | 1.30 (s) (CH$_3$)$_3$C |
| 68 | 4.53 (d) | 3.60 (s) COOCH$_3$ |
| 70 | 4.10 (q) | 5.90 (m) H—CF$_2$— |
| 73 | 4.10 (q) | 3.40 (m) C5—H |
| 107 | 4.50 (d) | 3.75 (m) C5—H |
| 113 | 4.53 (d) | 3.60 (s) COOCH$_3$ |
| 131 | 4.55 (d) | 7.10 (d) H$_{arom.}$ |
| 132 | 4.56 (d) | 3.60 (s) COOCH$_3$ |
| 135 | 4.55 (d) | 3.68 (s) COOCH$_3$ |
| 140 | 4.58 (d) | 7.30 (m) H$_{arom.}$ |
| 147 | 4.55 (d) | 7.9 (s) H$_{arom.}$ |

| | |
|---|---|
| 2 | 3.59 (s, 3H); 3.82 (s, 3H); 4.52 (d, 2H); 6.87 (m, 2H); 7.15 (m, 2H) |
| 4 | 1.20 (t, 3H); 1.34 (t, 3H); 3.60 (s, 3H); 3.83 (s, 3H); 4.11 (m, 2H) |
| 12 | 3.8 (s, 3H); 4.6 (d, 2H); 6.85 (m, 3H); 7.3 (m, 1H) |
| 13 | 3.8 (s, 3H); 4.1 (q, 2H); 6.85 (m, 3H); 7.3 (m, 1H) |
| 21 | 0.98 (t, 3H); 3.6 (s, 3H); 4.53 (d, 2H); 7.55 (m, 2H); 8.09 (m, 2H) |
| 22 | 1.18 (t, 3H); 1.36 (t, 3H); 3.6 (s, 3H); 4.13 (q, 2H); 7.50 (m, 2H), 8.09 (m, 2H) |
| 23 | 1.18 (t, 3H), 3.59 (s, 3H), 4.52 (d, 2H), 7.48 (m 2H); 8.08 (m, 2H) |
| 24 | 0.98 (t, 3H), 1.36 (t, 3H); 4.10 (q, 2H); 7.52 (m, 2H); 8.09 (m, 2H) |
| 82 | 1.14 (t, 3H), 1.30 (t, 3H); 4.08 (q, 2H); 4.64 (d, 2H); 6.89 (d, 2H); 7.13 (d, 2H) |
| 84 | 0.98 (t, 3H); 1.14 (t, 3H); 3.98 (t, 2H); 4.61 (d, 2H); 6.84 (d, 2H); 7.09 (d, 2H) |
| 90 | 1.0 (t, 3H); 1.32 (t, 3H); 1.75 (d, 3H); 4.10 (q, 2H), 4.50 (m, 2H); 5.76 (m, 2H) |
| 91 | 1.02 (t, 3H); 1.78 (d, 3H); 4.54 (m, 4H); 5.80 (m, 2H); 6.7–7.4 (m, 4H) |
| 101 | 0.96 (t, 3H); 1.30 (t, 3H); 2.68 (s, 3H); 4.04 (q, 2H); 7.36 (d, 2H); 7.58 (d, 2H) |
| 121 | 0.98 (t, 3H); 1.32 (t, 3H); 3.90 (s, 6H); 4.12 (q, 2H); 6.80 (m, 3H) |
| 123 | 1.18 (t, 3H); 3.89 (s, 6H); 4.57 (d, 2H); 6.81 (m, 3H) |
| 143 | 0.98 (t, 3H); 2.22 (s, 3H); 3.81 (s, 3H), 4.56 (d, 2H); 6.7–7.15 (m, 3H) |
| 144 | 0.98 (t, 3H); 1.31 (t, 3H); 2.22 (s, 3H); 3.80 (s, 3H); 4.11 (q, 2H), 6.7–7.25 (m, 3H) |
| 169 | 0.98 (t, 3H); 3.38 (s, 3H); 4.44 (s, 2H); 4.56 (d, 2H); 7.24 (d, 2H); 7.33 (d, 2H) |
| 170 | 0.98 (t, 3H); 1.32 (t, 3H); 3.38 (s, 3H); 4.13 (q, 2H); 4.44 (s, 2H); 7.24 (d, 2H); 7.33 (d, 2H) |
| 179 | 2.93 (m, 2H); 4.5 (m, 2H); 5.7 (m, 2H); 6.7–7.4 (m, 4H) |
| 184 | 0.95 (t, 3H), 2.93 (t, 2H); 4.48 (d, 2H); 5.3 (m, 2H); 5.9 (m, 1H) |

| | |
|---|---|
| 190 | 1.0 (t, 3H); 1.35 (t, 3H); 2.6 (s, 3H); 7.9 (d, 2H). |

The cyclohexane-1,3-dione derivatives of the formula I, and salts thereof, may be applied for instance in the form of directly sprayable solutions, powders suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, and N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthaleneslfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound No. 109 is mixed with 10 parts by weight of N-methyl-alpha-pyrrolidone. A mixture is obtained which is suitable for application in the form of very fine drops.

II. 20 parts by weight of compound No. 162 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound No. 52 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound No. 167 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound No. 62 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound No. 166 is intimately mixed with 97 parts by weight of particulate kaolin. A dust is obtained containing 3% by weight of the active ingredient.

VII. 30 parts by weight of compound No. 175 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound No. 171 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or agents containing them, may be applied pre- or postemergence. If certain crop plants tolerate the active ingredients less well when they are applied postemergence, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combated and their growth stage, and varies from 0.025 to 4 kg/ha and more, but is preferably from 0.1 to 3 kg/ha.

The herbicidal action of the cyclohexane-1,3-dione derivatives of the formula I is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the postemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The soybean plants were grown in a peat-enriched substrate. For this treatment, either plants which had been sown directly in the pots and grown there were selected, or plants which had been grown from seedlings and were transplanted to the pots a few days before treatment. The application rates for postemergence treatment varied from 0.125 for 1.0 kg of active ingredient per hectare.

The pots were set up in the greenhouse - species from warmer areas at from 20° to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were *Alopecurus myosuroides, Avena fatua, Beta vulgaris, Echinochloa crus-galli, Glycine max., Gossypium hirsutum, Hordeum vulgare, Lolium multiflorum, Oryza sativa, Setaria italica, Sorghum halepense,* and *Triticum aestivum.*

The compounds used for comparison purposes were 2-(1-allyloxy-butylidene)-5-(4-methoxyphenyl)-cyclohexane-1,3-dione (A) and 2-(1-ethoxyaminopropylidene)-5-(4-methylphenyl)-cyclohexane-1,3-dione (B) disclosed in German Laid-Open Application DE-OS 2,439,104.

On preemergence application in the greenhouse, for example compounds Nos. 20, 52, 61, 175, 123, 76, 122, 121, 154, 151, 149, 156, 166, 165, 164, 163, 162, 73, 96, 87, 86, 140, 139, 142, 167, 169, 170, and 171, at 3.0 kg/ha, had a significant herbicidal action on grass species.

In postemergence experiments, for example compounds No. 171 at 0.5 kg/ha and No. 53 at 1.0 kg/ha selectively combated unwanted grasses in the cereal crop barley. Compounds Nos. 62 and 175, at 0.125 kg/ha, combated unwanted grasses in wheat without damaging the crop plants, whereas comparative agent A, at the same application rate, had a weaker action on unwanted grasses and also damaged the crop plant. At application rates of 0.25 and 1.0 kg/ha, for example compounds Nos. 60, 61, 79, 80 and 85, with a comparable action to comparative agent A on unwanted grasses, were tolerated better by wheat. In comparison to prior art active ingredient B, for instance compound No. 109 is extremely selective in barley and wheat.

For combating unwanted grasses in broadleaved crops such as sugarbeets and cotton, for example compounds Nos. 52, 86 and 87 are suitable applied postemergence at a rate of 0.5 kg/ha. Compounds Nos. 101, 162, 166, 167, 168 and 169, applied postemergence at 0.5 kg/ha, are effective on unwanted grasses and are selective in soybeans.

In view of the tolerance of the various application methods, the herbicides according to the invention may be used in a further large number of crops for removing unwanted wild grasses or grassy crop plants growing where they are not desired.

The following crops may be mentioned by way of example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rapeseed |
| *Brassica napus* var. *napobrassica* | |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |

| Botanical name | Common name |
| --- | --- |
| Helianthus tuberosus | |
| Hevea brasiliensis | rubber plants |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Phaseolus lunatus | limabeans |
| Phaseolus mungo | mungbeans |
| Phaseolus vulgaris | snapbeans, green beans, dry beans |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize (post-directed only |

To increase the spectrum of action and to achieve synergistic effects, the cyclohexane-1,3-dione derivatives of the formula I, or agents containing them, may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, triazinones, uracils, benzofuran derivatives, other cyclohexane-1,3-dione derivatives, etc.

It may also be useful to apply the novel compounds, or herbicidal agents containing them, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies.

We claim:

1. A cyclohexane-1,3-dione derivative of the formula

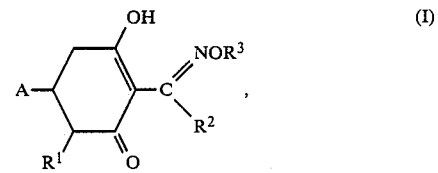

where A is phenyl monosubstituted in the para-position by trifluoromethyl, by fluorine-substituted $C_1$–$C_3$-alkoxy or by $C_3$–$C_5$-alkynyloxy, $R^1$ is hydrogen, methoxycarbonyl, ethoxy-carbonyl, methyl or cyano, $R^2$ is $C_1$–$C_4$-alkyl, and $R^3$ is $C_1$–$C_3$-alkyl, $C_3$- or $C_4$-alkenyl, $C_3$- or $C_4$-haloalkenyl having 1, 2 or 3 halogen substituents, or propargyl, or a salt thereof.

2. A cyclohexane-1,3-dione derivative of the formula I as defined in claim 1, where A is phenyl substituted in the ortho-, meta- or para-position by fluorine-substituted $C_1$–$C_3$-alkoxy or by $C_3$–$C_5$-alkynyloxy.

3. A cyclohexane-1,3-dione derivative of the formula I as claimed in claim 1, where A is trifluoromethyl-substituted phenyl.

4. A cyclohexane-1,3-dione derivative of the formula I as defined in claim 1, where $R^1$ is hydrogen.

5. A cyclohexane-1,3-dione derivative of the formula I as defined in claim 1, where A is 4-trifluoromethylphenyl, $R^1$ is hydrogen, $R^2$ is n-propyl and $R^3$ is ethyl.

6. A herbicide containing inert additives and a herbicidally effective amount of a cyclohexane-1,3-dione derivative of the formula I, or a salt thereof, as defined in claim 1.

7. A herbicide as defined in claim 6, containing from 0.1 to 95 wt% of a cyclohexane-1,3-dione derivative of the formula I or a salt thereof.

8. A herbicide as defined in claim 6, containing a cyclohexane-1,3-dione derivative of the formula I where A is trifluoromethyl-substituted phenyl.

9. A process for combating the growth of grasses wherein the grasses and/or the area to be kept free from grasses are treated with a herbicidally effective amount of a cyclohexane-1,3-dione derivative of the formula I as defined in claim 1.

10. A cyclohexane-1,3-dione derivative as defined in claim 1, wherein A is phenyl substituted in the para-position by difluoromethoxy.

* * * * *